United States Patent [19]

Gerberich, Jr.

[11] 4,054,590
[45] Oct. 18, 1977

[54] PRODUCTION OF FATTY ACIDS

[75] Inventor: Harold Robert Gerberich, Jr., Corpus Christi, Tex.

[73] Assignee: Celanese Corporation, New York, N.Y.

[21] Appl. No.: 724,034

[22] Filed: Sept. 17, 1976

Related U.S. Application Data

[63] Continuation-in-part of Ser. No. 586,761, June 13, 1975, abandoned.

[51] Int. Cl.$^2$ .......... C07C 51/20; C07C 51/24; C07C 51/26; C07C 51/28
[52] U.S. Cl. .......... 260/413; 260/530 R; 260/531 R; 260/540; 260/541
[58] Field of Search .......... 260/413, 419, 533 R, 260/530 R, 531 R, 540, 541

[56] References Cited

U.S. PATENT DOCUMENTS

| 1,721,959 | 7/1920 | James | 260/413 |
| 2,698,336 | 12/1954 | Nelson | 260/419 |
| 2,969,380 | 1/1961 | Selwitz | 260/413 |
| 3,646,078 | 2/1972 | Fanning | 260/413 |
| 3,775,450 | 11/1973 | Washecheck et al. | 260/419 |

FOREIGN PATENT DOCUMENTS

| 1,136,322 | 9/1962 | Germany | 260/413 |
| 202,108 | 9/1967 | U.S.S.R. | 260/419 |
| 165,442 | 11/1971 | U.S.S.R. | 260/419 |

Primary Examiner—Winston A. Douglas
Assistant Examiner—P. E. Konopka
Attorney, Agent, or Firm—Stewart N. Rice; Ralph M. Pritchett

[57] ABSTRACT

A process for producing fatty acids from $C_{12}$ to $C_{35}$ normal alkanes by air oxidizing the alkanes, followed by nitric acid oxidation of the air oxidation product.

10 Claims, No Drawings

PRODUCTION OF FATTY ACIDS

BACKGROUND OF THE INVENTION

This is a continuation-in-part of U.S. patent application Ser. No. 586,761, filed June 13, 1975, now abandoned.

The production of fatty acids from paraffins, especially $C_{12}$ to $C_{35}$ normal alkanes, by liquid phase oxidation with modecular oxygen is well known and has been commercially practiced for many years. The most usual way of recovering the fatty acids from the oxidate involves adding a caustic solution to convert the fatty acids to sodium salts followed by "springing" the fatty acids with sulfuric acid. The cost of caustic and sulfuric is a substantial expense in these processes. Other methods for treating the oxidate of the liquid phase oxidation have been proposed, one such method being that proposed in U.S. Pat. No. 2,969,380 issued Jan. 24, 1961 to Charles M. Selwitz. This reference discloses a process wherein the product of the molecular oxygen oxidation is separated by saponification into various components, some of which (alcohols and Ketones) are further oxidized by nitric acid to produce additional fatty acids.

While the foregoing and other processes are effective in producing synthetic fatty acids, they have obvious drawbacks such as the cost of the alkali and acids for recovering the fatty acids. Alternative processes having only one oxidation step have relatively low efficiency. By the process of U.S. Pat. No. 2,969,380 a somewhat increased efficiency may be obtained by a secondary oxidation but not without expensive separations between oxidation steps. Two-stage oxidations (for example, air oxidation followed by nitric acid oxidation) for producing dicarboxylic acids from paraffins and which do not involve a separation between oxidation stages are known; however, none of these processes has been proposed for producing fatty acids as opposed to dicarboxylic acids. An example of such a process for production of dicarboxylic acids is disclosed in U.S. Pat. No. 2,978,473 issued Apr. 4, 1961, to H. Chafetz et al.

It is thus an object of the present invention to provide a method of producing fatty acids from alkanes whereby increased efficiency may be obtained. It is an additional object of the present invention to provide a method of producing fatty acids from alkanes which does not require the use of alkali for recovery. It is a further object of the present invention to provide a process for producing fatty acids from alkanes involving primary and secondary oxidations without the necessity of separation of components between oxidation steps. Additional objects will become apparent from the following description of the present invention.

SUMMARY

The foregoing and additional objects are accomplished by the present invention which in one of its aspects is an improvement in a process for the production of fatty acids from $C_{12}$ to $C_{35}$ normal alkanes wherein said alkanes are oxidized in the liquid phase with molecular oxygen at elevated temperatures and pressures sufficient to maintain a liquid phase of said alkanes for a time whereby there is produced a crude primary oxidate liquid product having a saponification number of less than 95 and containing fatty acids, unreacted alkanes and oxygenated hydrocarbon intermediates, and wherein a fatty acid product is recovered from said crude primary oxidate liquid product, which improvement comprises: in a secondary oxidation oxidizing the said crude primary oxidate liquid product prior to recovery of any fatty acids therefrom by nitric acid oxidation at elevated temperatures and pressures sufficient to maintain a liquid phase, and in the presence of a catalytic amount of a nitric acid oxidation catalyst, to produce a crude secondary oxidate liquid product comprised of an aqueous phase containing most of the $C_1$ to $C_6$ fatty acids and a hydrocarbon phase containing most of the $C_7$ and higher fatty acids, followed by recovery of a fatty acid product from said crude secondary oxidate liquid product.

DETAILED DESCRIPTION OF THE INVENTION

The present invention is applicable to the production of fatty acids from a $C_{12}$ to $C_{35}$ normal alkane, that is a straight-chain alkane containing from 12 to 35 carbon atoms. Usually a mixture of alkanes will be utilized, however, a single alkane may be utilized as feed if desired. By the term "fatty acids" is meant those straight-chain monocarboxylic acids free of unsaturation, that is straight-chain monocarboxylic alkanoic acids. The fatty acids produced according to the present invention may contain from 1 to 35 carbon atoms although most will be within the range of 2 to 25 carbon atoms.

The first step in the process for the production of a fatty acid is the liquid phase oxidation of the alkane in the presence of molecular oxygen, which as pointed out above is well known in the prior art. This oxidation will sometimes hereinafter be referred to as the "air oxidation" since air is generally utilized as the source of molecular oxygen for economic reasons, although other sources of molecular oxygen may be used such as oxygen-enriched air or technically pure oxygen itself. The temperatures involved in the air oxidation may vary widely, for example, within the range of 100° to 300° C but are preferably within the range of about 110° to 140° C. The pressure needs to be only sufficient to maintain a liquid phase of the alkanes which, of course, will vary according to the temperature utilized. Generally, pressures within the range of about 1 to 200 atmospheres absolute may be utilized although pressures within the range of about 1 to 20 atmospheres absolute are preferred and are more economical. Atmospheric pressure is especially preferred.

The air oxidation may be accomplished either with or without a catalyst, although it is preferable to use an oxidation catalyst of any of the well known types generally employed in an oxidation utilizing molecular oxygen. Catalyst systems include those containing cobalt, manganese, potassium, chromium, nickel, or copper or mixtures thereof. A catalyst containing both potassium and manganese is preferred, potassium permanganate being a suitable source of such a catalyst. These catalysts are generally utilized such that the catalyst metals are present in an amount of from about 10 to 10,000 parts per million, preferably about 100 to 1,500 parts per million, by weight of the weight of the reaction mixture. The air oxidation may be carried out in the presence of a solvent, if desired, but such is not preferred because of the cost of recovering and recycling the solvent. Suitable solvents include the $C_2$ to $C_4$ fatty acids such as acetic, propionic and butyric, with acetic being preferred.

Residence or reaction times vary according to temperature, pressure, feed composition and the like, but are generally on the order from 0.5 to 20 hours, more usually from about 2 to 10 hours. The reaction should be carried out for a time such that the saponification number of the crude primary oxidate liquid product does not exceed about 95. Generally, the saponification number should be less than 95, for example 50 to 95, but preferably should be less than about 80, preferably about 60 to 75. Dicarboxylic acids instead of fatty acids will be produced if high saponification numbers are obtained. The saponification number is the milligrams of potassium hydroxide required per gram of product to neutralize any free acids and carboxyl groups tied up as esters. It may be determined by ASTM Method of Tests D1962-61. In conducting the air oxidation, the air is preferably sparged through the liquid reaction mixture to obtain the desired contact. Such also provides agitation which is desirable.

A crude primary oxidate liquid product will be produced as the product of the air oxidation. This crude primary oxidate liquid product is a two phase liquid which contains a wide mixture of compounds including fatty acids ranging from $C_1$ to $C_{35}$ acids and also includes oxygenated hydrocarbon intermediates and some unreacted alkanes. Also present will be any catalyst utilized in the air oxidation. One phase is an aqueous phase containing most of the $C_1$ to $C_6$ fatty acids and the other phase is a non-aqueous or hydrocarbon phase containing unoxidized alkane hydrocarbons and the higher fatty acids (for example, $C_7$ and above). Both phases also contain oxygenated hydrocarbon intermediates.

In the prior art, the fatty acid products were usually recovered from the liquid product of the air oxidation via saponification, esterification or the like without further oxidation, although as pointed out above it was also known to effect a separation of the air oxidation product into components and further oxidize some of these components. However, according to the present invention, the entire crude primary oxidate liquid without the separation of any components therefrom is subjected to a nitric acid oxidation prior to recovery of the ultimate fatty acid product. It is not necessary to effect any separation of components, removal of catalyst or the like. Conventional nitric acid oxidation techniques may be utilized and this will generally involve mixing the product of the air oxidation with from about 0.1 to 10 times, preferably about 0.5 to 3.0 times, its weight of an aqueous nitric acid solution. The aqueous nitric acid solution will generally be of a concentration of about 40 to 70 percent by weight nitric acid. There will also be added a nitric acid oxidation catalyst, practically any of the known oxidation catalysts such as those containing cobalt, nickel, iron, chromium, manganese, copper or vanadium or mixtures thereof. Preferred is a copper-vanadium catalyst, such usually being added as ammonium metavanadate and copper turnings. The total amount of catalyst metals should generally be within the range of about 0.1 to 1.0 percent by weight of the reaction mixture. The nitric acid oxidation may take place in one reactor or a plurality in series.

Temperatures for the nitric acid oxidation should generally range from about 60° to 130° C and preferably within the range of about 75° to 90° C. The pressure needs to be only sufficient to maintain a liquid phase and generally would be within the range of about 1 to 20 atmospheres absolute, preferably about 1 to 5 atmospheres absolute. Since the reaction mixture in the nitric acid oxidation will be a two-phase system, agitation of the reaction mixture will provide improved results. It is also recommended that an inert purge gas be used to remove the nitrogen oxide gases which are generated in the nitric acid oxidation so as to prevent undue nitration of the fatty acids present in the reaction mixture. This may be accomplished by merely blowing the purge gas through the gaseous atmosphere above the liquid reaction mixture but is preferably accomplished by sparging of the purge gas through the liquid reaction mixture so as to aid in the agitation thereof. By "inert" is meant that the purge gas is inert under the conditions of the nitric acid oxidation such that it does not react to any substantial extent with itself or with the components of the reaction mixture of the nitric acid oxidation. Air is a suitable purge gas as is nitrogen.

The purpose of the nitric acid oxidation is to oxidize any partially oxidized alkanes, that is those which have not been oxidized to such an extent as to form a carboxylic acid and which are herein referred to as oxygenated hydrocarbon intermediates, to fatty acids which were not so oxidized in the air oxidation step. The effluent or product of the nitric acid oxidation will be a crude secondary oxidate liquid which will be a two phase system containing fatty acids, water, unreacted alkanes, nitrogen-containing impurities, various oxygenated compounds other than fatty acids, and the like. A fatty acid product may be recovered from this crude secondary oxidate liquid by known methods which may include subsequent purification steps. The liquid nitric acid oxidation product will consist of an aqueous nitric acid phase containing most of the $C_1$ to $C_6$ fatty acids and a non-aqueous or hydrocarbon phase containing most of the higher fatty acids (i.e. $C_7$ and above). In order to recover the fatty acid product, these two phases are preferably separated. The two phases may easily be separated at the temperature of the nitric acid oxidation, or if desired may be cooled prior to separation. Fatty acids may be recovered from the aqueous nitric acid phase by solvent extraction, such as with benzene, cyclohexane or the like followed by evaporation of the solvent.

The method of recovering the higher fatty acids from the hydrocarbon phase may be accomplished by addition of an excess of an aqueous caustic solution to convert the fatty acids to sodium salts followed by separation of the aqueous solution of the sodium salts and then "springing" the fatty acids by addition of sulfuric acid. The fatty acids are then further purified by vacuum distillation. Esterification techniques may also be used for recovery. While esterification or saponification are traditional methods of recovery for fatty acids, they are not the most economical. It has been discovered that solvent extraction may be used in lieu of the traditional methods of recovering the higher fatty acids. A wide variety of solvents will accomplish the extraction such as the lower alkanols, lower dialkyl ethers, lower dialkyl ketones, and aqueous solutions thereof. By the term "lower" in reference to alkanols, dialkyl ethers and dialkyl ketones is meant those wherein the alkyl groups are from one to four carbon atoms. Particular compounds include methanol, ethanol, n-butanol, diethyl ether, methyl ethyl ether, di-butyl ether, acetone, methyl ethyl ketone, di-n-propyl ketone and the like. Alcohols, however, have the disadvantage of forming esters with fatty acids due to trace amounts of nitric acid usually present which serves as a catalyst for the esterification. The preferred solvent is a mixture of a lower dialkyl ketone and water, especially acetone and water. The volume ratio of ketone to water may vary widely, for example, from about 1:1 to 7:1, although preferably from about 1.5:1 to 6:1. Sufficient water must be present to effect separation of the hydrocarbon-rich and acetone-rich phases, although too much water will result in difficult extraction of fatty acids. To minimize the extraction of hydrocarbons in a continuous extraction process, a duel solvent extraction may be utilized wherein a short chain hydrocarbon (preferably $C_7$ to $C_{11}$ alkanes, preferably normal alkanes) is fed countercurrent to the acetone-rich phase to displace the higher molecular weight hydrocarbon. The acetone, water and short chain hydrocarbon may then be distilled away from the fatty acids and the latter further purified by vacuum distillation.

Where only a single solvent system is used (such as an acetone-water solvent) the hydrocarbon phase of the nitric acid oxidation product may be introduced to the lower section of a column and the acetone-water or other solvent introduced to the upper end of the column. Removed overhead will be a hydrocarbon phase and removed from the lower end of the column will be the extracted aqueous phase containing fatty acids as well as a small amount of hydrocarbons. Part of these hydrocarbons will be low boilers which are relatively easily removed by distillation although some high boilers will also be present. By use of a dual solvent extraction wherein the hydrocarbon phase of the nitric acid oxidation is fed to the midpoint of the column, the acetone-water solvent fed to the upper end of the column, and the short chain hydrocarbon solvent fed to a lower section of the column, the amount of high boiler hydrocarbons in the extracted aqueous phase may be reduced considerably.

The fatty acid product recovered from a process having a nitric acid oxidation step, unless subsequent purification techniques are utilized, may contain amounts of nitrogen-containing compounds as impurities. For many uses of the fatty acids, these nitrogeneous impurities must be substantially eliminated and it is known to accomplish such by mildly hydrogenating the nitrogen compounds to amines which are relatively easily removable. The hydrogenation of the fatty acid product or at least those fatty acids from the hydrocarbon phase may be conducted according to known hydrogenation procedure. It can advantageously be carried out by feeding the material to be hydrogenated together with hydrogen to a reaction zone maintained at a temperature within the range of about 50° to 300° C, preferably about 100° to 250° C, and a pressure within the range of about 1 to 200 atmospheres absolute, preferably 50 to 150 atmospheres absolute.

The hydrogenation should be conducted in the presence of a hydrogenation catalyst, substantially any of the known hydrogenation catalysts being operable. Suitable hydrogenation catalysts include those of copper, copper chromite, nickel, cobalt, platinum, or palladium or mixtures thereof. Preferred catalysts are those of platinum or palladium or mixtures thereof. The catalyst may be unsupported or supported on a known support such as carbon, and the like. The hydrogenation may be carried out in conventional fashion as in a fixed, flooded catalyst bed, a slurry catalyst bed, or a trickle catalyst bed.

Following the hydrogenation of the fatty acid product, the amines formed in the hydrogenation may be removed by conventional and known techniques to result in a fatty acid product of improved purity. For example, the amines may be removed by reaction with an aqueous solution of a strong acid to form an amine salt which will concentrate in the resulting aqueous phase. Suitable acids for such purpose include phosphoric, sulfuric and hydrochloric. An alternative method of amine removal is by ion exchange means wherein the amine-containing fatty acids are passed through a bed of a strong acid ion exchange resin. Use of an ion exchange resin avoids the possibility of emulsion formation which can occur when an aqueous solution of a strong acid is used. Other purification techniques are known and may be used.

The following examples are given to illustrate the invention but are not to be interpreted as limiting the scope thereof.

EXAMPLE I

To a continuous reactor were fed 368 liters (measured at STP) per hour of air, 1.0 liter (liquid) per hour of a mixture of $C_{20}$-$C_{22}$ normal alkanes and 0.39 grams per hour of potassium permanganate catalyst. The average residence time was 8 hours and the reaction temperature and pressure were 122° C and 2.36 atmospheres absolute, respectively. Analysis of the recovered product showed that 42 mole percent of the hydrocarbon had been oxidized with 39 mole percent having been converted to monocarboxylic acids. The product had a saponification number of 90 mg. KOH per gram as defined hereinabove, and an acid number of 57. The remaining product was aldehydes, ketones, alcohols, carbon oxides, and multifunctional compounds.

Both phases of oxidation product (500 cc.) were added over a 20 minute period to 1,000 cc. of 70 weight percent nitric acid containing 2.0 grams of ammonium metavanadate ($NH_4VO_3$) and 1.0 gram of copper (II). The temperature was maintained at 80°-85° C during the period of addition and for 1 hour afterwards. The product phases were separated and the hydrocarbon phase washed with water to remove nitric acid and soluble nitrogen oxides. Analysis of both product phases of the nitric acid oxidation product showed that as a result of the nitric acid oxidation the effective molar efficiency of monocarboxylic acids was increased to 75% based on the fraction of hydrocarbon oxidized in the air oxidation step.

The hydrocarbon phase (500 cc.) containing the $C_7$ and above monocarboxylic acids was then extracted five times at 25° C with 310 cc. portions of a solution of 70 parts acetone and 30 parts water by volume. After removal of the acetone and water by distillation, 85 grams of $C_7$-$C_{21}$ fatty acid product having a paraffin content of 6.8 weight percent were recovered.

The aqueous nitric acid phase (1,000 cc.) was extracted four times at 25° C with 500 cc. portions of benzene. After removal of benzene by distillation, 8.8 grams of $C_2$ to $C_6$ fatty acids were recovered.

The next example illustrates the use of dual solvent extraction to reduce the paraffin content of recovered $C_7$-$C_{21}$ fatty acids.

EXAMPLE II

The hydrocarbon phase from the nitric acid oxidation described in Example I was fed to the 8th stage (measured from the top) of a 17 stage continuous extraction column at a rate of 6.9cc/min. At the same time, a solution of 70 parts acetone and 30 parts water by volume was fed to the top of the extraction column at a rate of 19.4cc/min. and n-heptane was fed to the 17th stage (measured from the top) at a rate of 5.3cc/min. The acetone-water phase was removed from the bottom of the extractor at a rate of 21.4cc/min. and the hydrocarbon phase from the top at a rate of 10.4cc/min.

After removal of acetone, water, and n-heptane from the bottom phase by distillation, the recovered $C_7$-$C_{21}$ fatty acids were found to contain 3.6 weight percent paraffins.

The embodiment of the invention in which an exclusive property or privilege is claimed are defined as follows:

1. In a process for the production of fatty acids from $C_{12}$ to $C_{35}$ normal alkanes wherein said $C_{12}$ to $C_{35}$ normal alkanes are oxidized in the liquid phase with molecular oxygen at elevated temperatures and pressures sufficient to maintain a liquid phase of said alkanes for a time whereby there is produced a crude primary oxidate liquid product containing fatty acids, unreacted alkanes and oxygenated hydrocarbon intermediates, and wherein a fatty acid product is recovered from said crude primary oxidate liquid product, the improvement which comprises: controlling said oxidation with molecular oxygens at a level such that said crude primary oxidate has a saponification number of about 50 to 95 and, in a secondary oxidation, oxidizing said crude primary oxidate liquid product prior to recovery of any fatty acids therefrom by nitric acid oxidation at elevated temperatures and pressures sufficient to maintain a liquid phase, and in the presence of a catalytic amount of a nitric acid oxidation catalyst, to produce a crude secondary oxidate liquid product comprising an aqueous phase containing most of the $C_1$ to $C_6$ fatty acids and a hydrocarbon phase containing most of the $C_7$ and higher fatty acids, followed by recovering a fatty acid product from said crude secondary oxidate liquid product.

2. The process of claim 1 wherein the oxidation of said alkanes with molecular oxygen is accomplished utilizing a catalytic amount of an oxidation catalyst and at temperatures within the range of about 110° to 140° C, and wherein the saponification number of said crude primary oxidate liquid is less than about 80.

3. The process of claim 2 wherein said oxidation of said alkanes with molecular oxygen is accomplished utlizing an oxidation catalyst containing potassium or manganese or mixtures thereof.

4. The process of claim 2 wherein said nitric acid oxidation is conducted with agitation at temperatures within the range of about 75° to 95° C and pressures within the range of about 1 to 20 atmospheres absolute.

5. The process of claim 4 wherein said nitric acid oxidation is conducted utilizing a catalyst containing copper or vanadium or mixtures thereof.

6. The process of claim 2 wherein the fatty acids contained in said hydrocarbon phase of said crude secondary oxidate liquid product are recovered therefrom by solvent extraction utilizing a solvent comprising an aqueous solution of a lower dialkyl ketone.

7. The process of claim 6 wherein said lower dialkyl ketone is acetone.

8. The process of claim 5 wherein the fatty acids contained is said hydrocarbon phase of said crude secondary oxidate liquid product are recovered therefrom by solvent extraction utilizing a solvent comprising an aqueous solution of a lower dialkyl ketone.

9. The process of claim 8 wherein said dialkyl ketone is acetone.

10. The process of claim 5 wherein recovery of the fatty acids from said hydrocarbon phase of said crude secondary oxidate liquid is accomplished by dual solvent extraction utilizing an aqueous solution of acetone as one solvent and a $C_7$ to $C_{10}$ normal alkane as the other solvent.

* * * * *